United States Patent
Wang et al.

(10) Patent No.: US 6,490,334 B1
(45) Date of Patent: Dec. 3, 2002

(54) METHODS AND APPARATUS FOR HIGH PITCH HELICAL COMPUTED TOMOGRAPHY IMAGE RECONSTRUCTION

(75) Inventors: Sharon X. Wang, Brookfield, WI (US); Thomas L. Toth, Brookfield, WI (US); Piero U. Simoni, New Berlin, WI (US); Stephen W. Metz, Greenfield, WI (US); Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/896,957

(22) Filed: Jun. 29, 2001

(51) Int. Cl.$^7$ ................................................. A61B 6/03
(52) U.S. Cl. ............................. 378/15; 378/19; 378/901
(58) Field of Search ........................... 378/4, 8, 15, 19, 378/901

(56) References Cited

U.S. PATENT DOCUMENTS

| | | | |
|---|---|---|---|
| 6,272,200 B1 * | 8/2001 | Pan et al. | 378/15 |
| 6,301,325 B1 * | 10/2001 | Besson et al. | 378/15 |
| 6,341,154 B1 * | 1/2002 | Besson | 378/15 |
| 6,411,670 B1 * | 6/2002 | Besson | 378/4 |

FOREIGN PATENT DOCUMENTS

EP 1 096 426 A1 5/2001

OTHER PUBLICATIONS

United States patent application No. 09/452,275 filed Dec. 29, 2000.

* cited by examiner

Primary Examiner—David V. Bruce
(74) Attorney, Agent, or Firm—Carl B. Horton, Esq.; Armstrong Teasdale LLP

(57) ABSTRACT

There is therefore provided, in one aspect, a method for imaging an object utilizing a computed tomographic (CT) imaging system having a rotating gantry, a multislice detector array on the rotating gantry and using at least n>1 rows of detector channels, and a radiation source on the rotating gantry configured to project a beam of radiation towards the multislice detector array through an object to be imaged. The method includes helically scanning the object with the CT imaging system at a pitch p>n to acquire projection data from the n rows of detector channels; applying a combined helical weight and conjugate weight to at least a portion of the acquired projection data to produce virtual projection data compensating for incomplete helical row data of the acquired projection data; and reconstructing an image of the object utilizing the acquired projection data and the virtual projection data.

28 Claims, 6 Drawing Sheets

METHODS AND APPARATUS FOR HIGH PITCH HELICAL COMPUTED TOMOGRAPHY IMAGE RECONSTRUCTION

BACKGROUND OF THE INVENTION

This invention relates generally to methods and apparatus for computed tomographic (CT) imaging, and more particularly to methods and apparatus for conversion of helical projection data into axial projection data for the reconstruction of sectional images.

Cardiac and many other new applications of computed tomographic (CT) imaging demand that multislice CT imaging systems produce high quality images with thinner slice profiles and faster coverage speeds than have been available in the past. To reduce the x-ray dose received by patients, it is desirable to increase the table speed of the CT imaging system. The higher table speed results in a higher helical pitch that often makes it impossible to use full scan algorithms because the data acquired spans a region less than $2\pi$. One solution is to utilize helical linear interpolation algorithms followed by application of Parker weights to the scan data for image reconstruction.

For example, an axial half-scan algorithm has been used for modes in which the helical pitch is p>n, where n is the number of image slices. The performance of such weighting functions (in terms of image quality) is satisfactory when helical pitch is low. However, artifacts and noise increase as the pitch increases.

For example, where a helical view-weight is followed by an axial half-scan weight, the axial half-scan weighting function has been used merely as a passive measure to eliminate data redundancy. Furthermore, a significant portion of data required for image reconstruction has to be obtained by extrapolation. Extrapolation results in increased artifacts and noise.

BRIEF SUMMARY OF THE INVENTION

There is therefore provided, in one aspect, a method for imaging an object utilizing a computed tomographic (CT) imaging system having a rotating gantry, a multislice detector array on the rotating gantry and utilizing at least n>1 rows of detector channels, and a radiation source on the rotating gantry configured to project a beam of radiation towards the multi slice detector array through an object to be imaged. The method includes helically scanning the object with the CT imaging system at a pitch p>n to acquire projection data from the n rows of detector channels; applying a combined helical weight and conjugate weight to at least a portion of the acquired projection data to produce virtual projection data compensating for incomplete helical row data of the acquired projection data; and reconstructing an image of the object utilizing the acquired projection data and the virtual projection data.

In another aspect, there is provided a computed tomographic (CT) imaging system having a rotating gantry, a multislice detector array on the rotating gantry and configurable to utilize at least n>1 rows of detector channels, and a radiation source on the rotating gantry configured to project a beam of radiation towards the multislice detector array through an object to be imaged. The imaging system is configured to helically scan the object at a pitch p>n to acquire projection data from the n rows of detector channels, apply a combined helical weight and conjugate weight to at least a portion of the acquired projection data to produce virtual projection data compensating for incomplete helical row data of the acquired projection data, and reconstruct an image of the object utilizing the acquired projection data and the virtual projection data.

In yet another aspect, there is provided a computer configured to read projection data obtained by helically scanning an object at a pitch p>n utilizing a computed tomographic imaging system using n rows of detector channels, apply a combined helical weight and conjugate weight to at least a portion of the acquired projection data to produce virtual projection data compensating for incomplete helical row data of the acquired projection data, and reconstruct an image of the object utilizing the acquired projection data and the virtual projection data.

In still another aspect, there is provided a computer readable medium having recorded thereon instructions configured to instruct a computer to read projection data acquired by helically scanning an object at a pitch p>n utilizing a computed tomographic imaging system using n rows of detector channels, apply a combined helical weight and conjugate weight to at least a portion of the acquired projection data to produce virtual projection data compensating for incomplete helical row data of the acquired projection data, and reconstruct an image of the object utilizing the acquired projection data and the virtual projection data.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
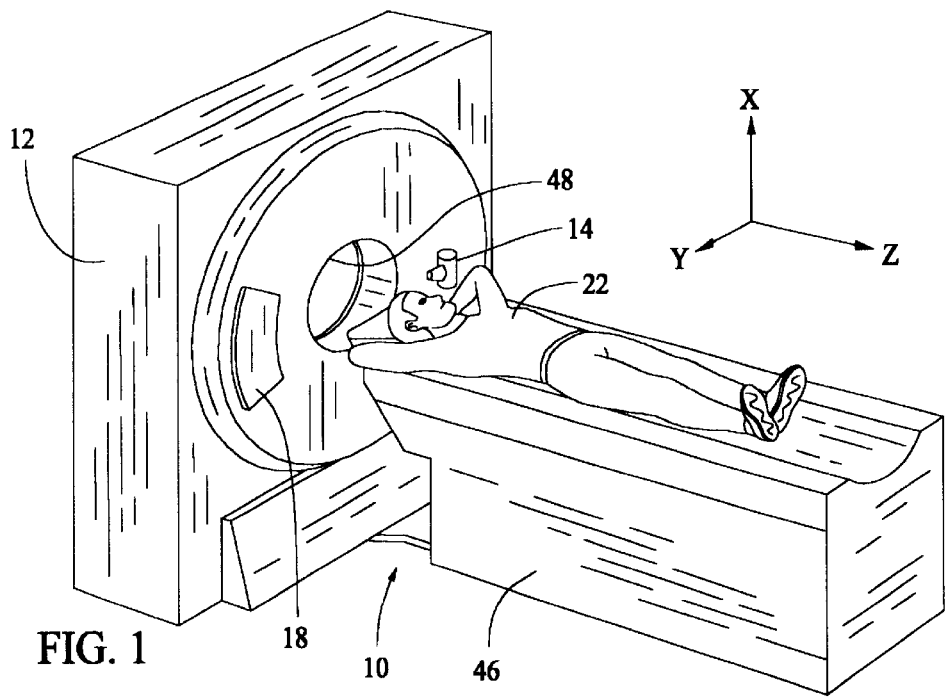
FIG. 1 is a pictorial view of a CT imaging system.
Figure 2:
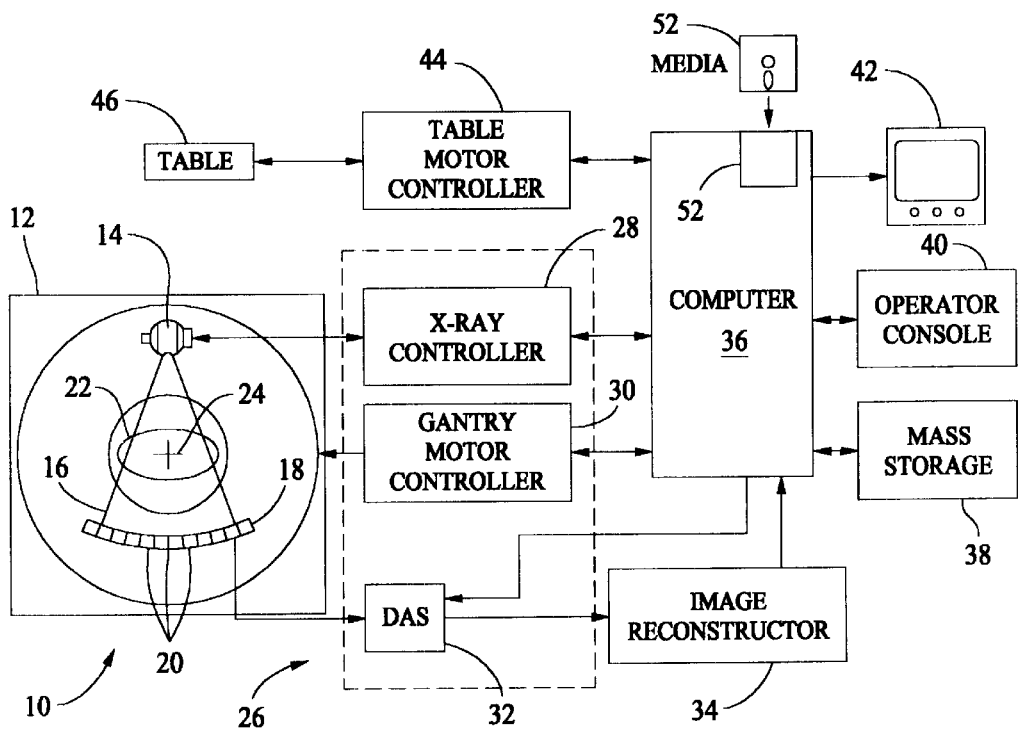
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Figure 3:
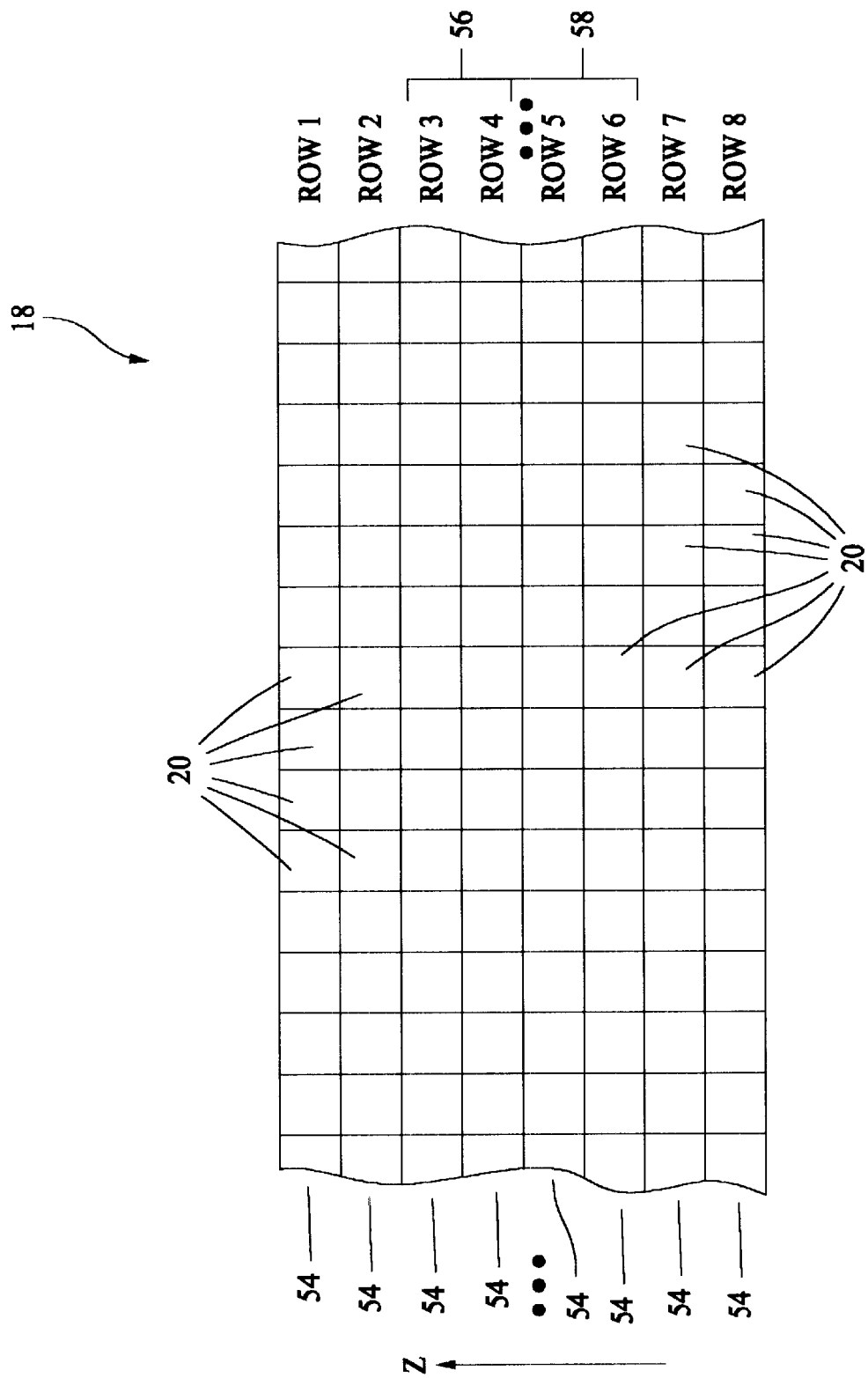
FIG. 3 is a simplified representation of a central portion of a multislice detector array utilized in one embodiment of the system illustrated in FIG. 1.

In one embodiment and referring to FIG. 3, outputs of detector elements 20 in adjacent rows 54 of detector array 18 are electronically combinable. More particularly, adjacent elements 20 are combinable in a z-direction (i.e., a direction parallel to an axis or rotation of gantry 12) so that imaging system 10 acquires data representative of thicker slices of object or patient 22 than when these outputs are not combined. Also in one embodiment, a selectable number of detector rows 54 of detector array 18 are used for acquisition of data. Thus, in some scans, not all rows 54 of detector elements 20 in detector array 18 are utilized. For this reason, as used herein, when outputs of detector elements 20 in adjacent rows 54 of detector array 18 are not electronically combined, a "row of detector channels" refers to a row 54 of detector elements utilized in a scan to acquire projection data. When outputs of detector elements 20 in adjacent rows 54 of detector array 18 are electronically combined, a "row of detector channels" as used herein refers to a row 56 of combined outputs.

For example, consider an embodiment in which detector array 18 has eight rows 54 of detector elements 20 (e.g., rows 1–8). If, for example, detector elements 20 in rows 3 and 4 are electronically combined in the z-direction, detector elements 20 in rows 5 and 6 are electronically combined in the z-direction, and detector rows 1, 2, 7, and 8 are not utilized to acquire data, imaging system 10 is said to be utilizing two rows 56, 58 of detector channels. Row 56 of detector channels 56 comprises combined rows 3 and 4 of detector elements 20. Row 58 of detector channels 58 comprises the combined rows 5 and 6 of detector elements 20. On the other hand, if detector elements 20 in eight-row detector array 18 are not combined, but only rows 2 through 7 are used to acquire data, imaging system 10 is said to be utilizing six rows 54 (i.e., rows 2 through 7, but not rows 1 and 8) of detector channels.

Figure 4:
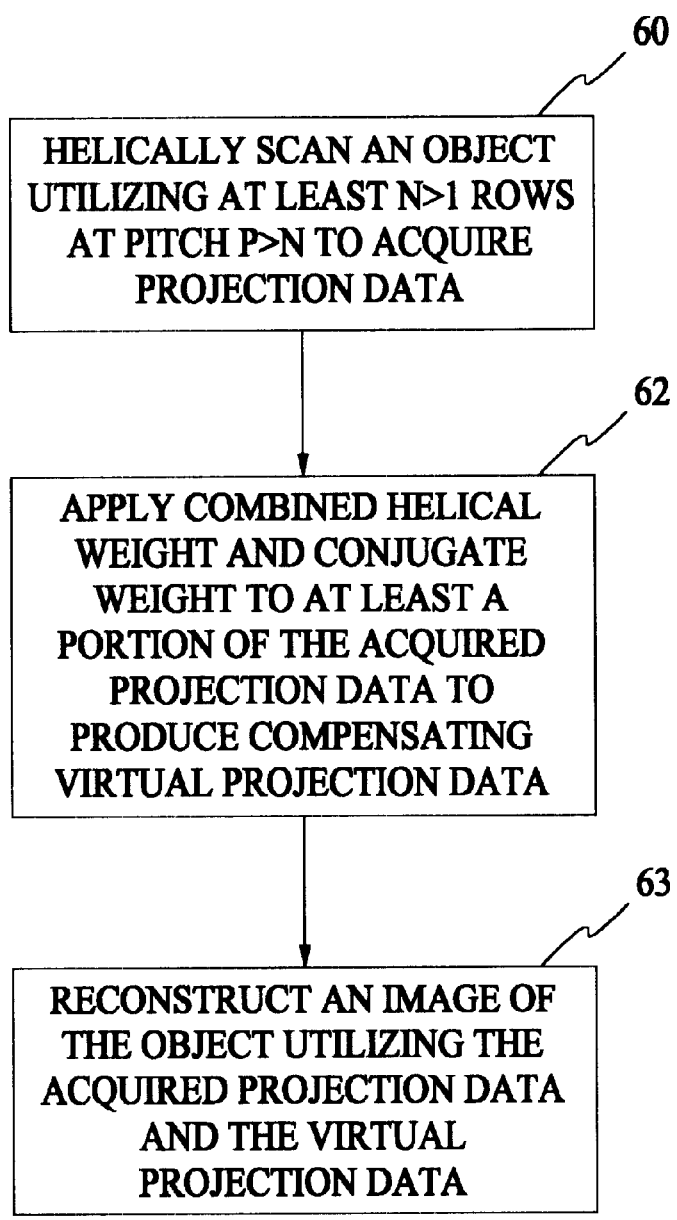
FIG. 4 is a simplified flow chart representation of one embodiment of a method of the present invention.

In one embodiment of the present invention and referring to FIG. 4, an object (e.g., object 22 of FIGS. 1 and 2) is helically scanned 60 utilizing at least n>1 rows (e.g., rows 54 or combined rows such as 56 and 58) of detector channels with the CT imaging system. A helical pitch p>n is used to acquire projection data from the n rows of detector channels. A combined helical weight and conjugate weight is applied 62 to at least a portion of the acquired projection data to produce virtual projection data compensating for incomplete helical row data of the acquired projection data. An image of the object is reconstructed 63 utilizing the acquired projection data and the virtual projection data.

Figure 5:
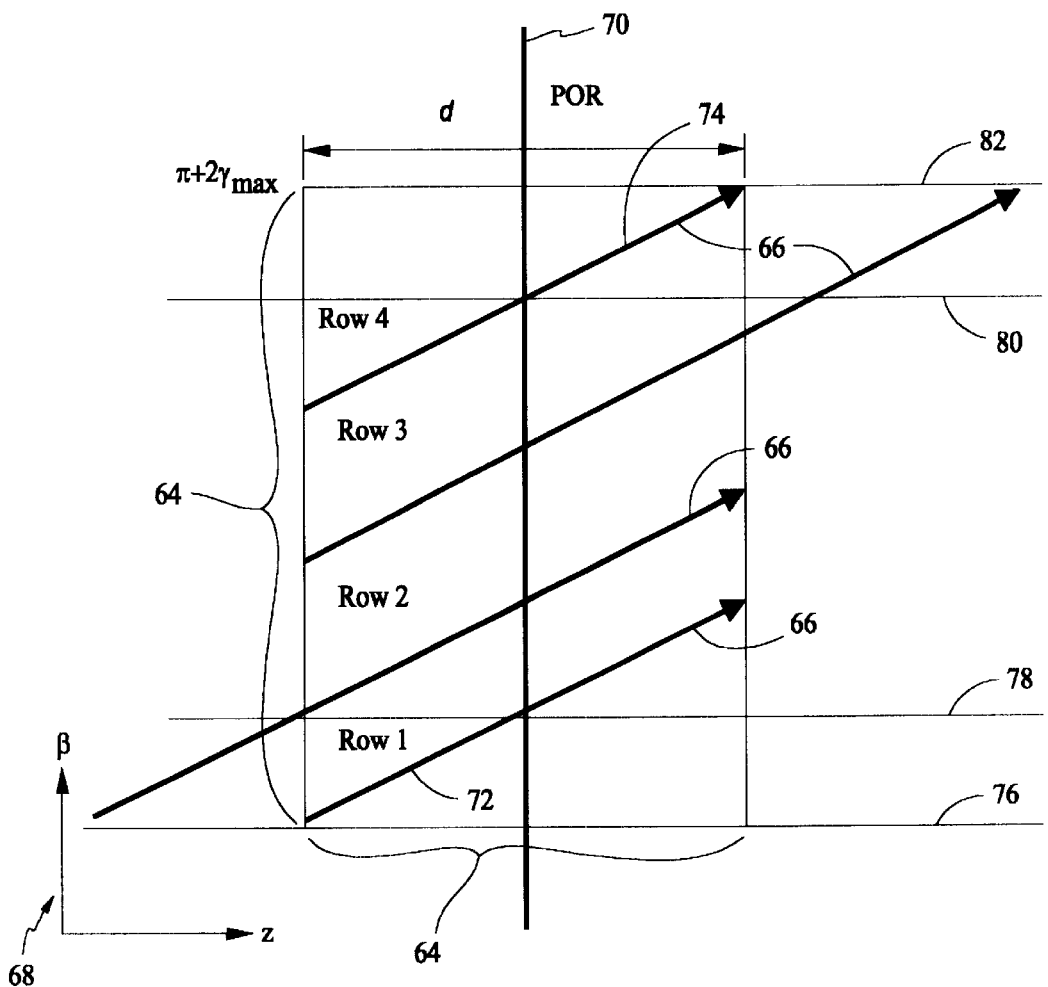
FIG. 5 is a simplified representation of an image reconstruction region showing trajectories of a multislice imaging scan.

Referring to FIG. 5, a representation of an image reconstruction region 64 is shown for a scan utilizing four rows of detector channels, along with trajectories 66 of the four rows of detector channels. Coordinate system 68 is defined such that the horizontal axis represents the table motion direction z, while the vertical axis represents the gantry rotation angle $\beta$. Centerline 70 represents the plane of reconstruction (POR).

When the $\beta$ angle of the scan data trajectory covers a region less than $2\pi$, there is only one data line at the beginning and end of the image reconstruction region. Single data lines 72 and 74 are bounded in the box between lines 76 and 78 and between 80 and 82 respectively. In these regions, there is not another row of helical data on the other side of POR 70, and interpolation is no longer possible. If extrapolation were employed to estimate the data along POR 70, data outside the image reconstruction region would have to be employed, which would introduce artifacts and noise and provide false information about the structure in the image reconstruction region. Use of eight rows of detector channels rather than four would result in more severe artifacts because the slope of data lines or trajectories 66 would be reduced. Therefore, more data from outside of the image reconstruction region would be needed for extrapolation.

Rather than extrapolate, one embodiment of the present invention uses a row-wise pitch method that integrates helical weighting with conjugate ray weighting to achieve high image quality. Well-defined conjugate rays are used to compensate for helical row data that are incomplete due to fast table motion. This embodiment provides a reduced artifact level, improved noise level, a better slice sensitivity profile (SSP), a nearly smooth weighting function in the γ direction for robust computation, and easy hardware implementation.

Figure 6:
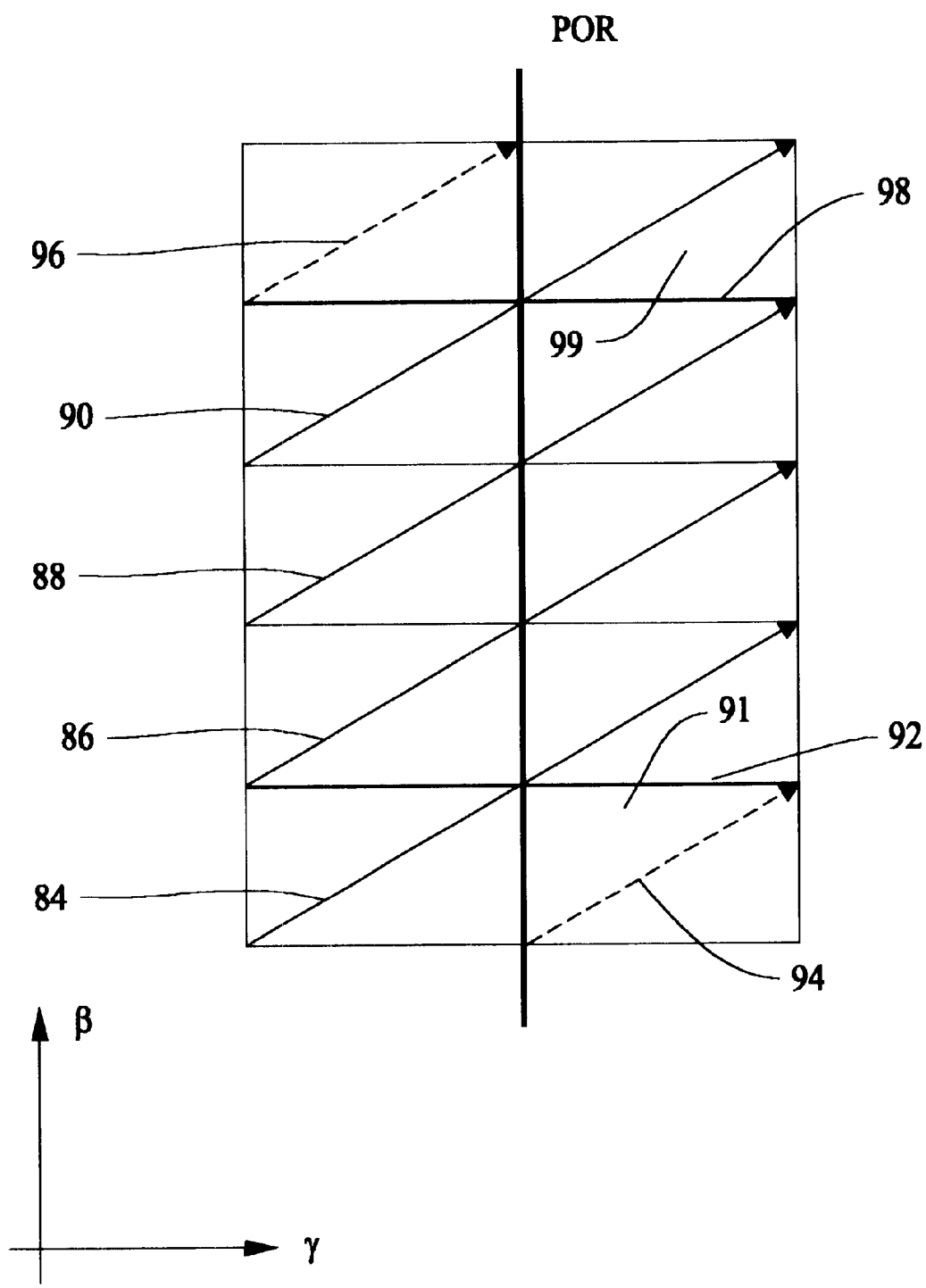
FIG. 6 is a representation of a virtual/real data distribution of a four slice (i.e., four detector channel row) CT imaging system in a high pitch mode.

FIG. 6 is a representation of a data distribution of a 4-slice CT imaging system (i.e., one operated with four rows of detector channels) in a high pitch mode. Lines 84, 86, 88, and 90 represent real data from detector channel rows 1, 2, 3, and 4, respectively, while dashed lines 94 and 96 represent virtual data. It can be seen that if virtual data 94 and 96 actually exist, they can be used to perform interpolation with real data and extrapolation can be avoided. In one embodiment of the present invention, helical weighted conjugate rays act as the virtual data. Because a center portion of the helical weighted data between 92 and 98 is considered as accurate axial data, utilization of these data produces high quality images. Although a small portion of conjugate data is needed in regions 91 and 99, embodiments of the present invention provide valid interpolation because the data are combined with data on the other side of POR 70. Thus, real and virtual data are always located on both sides of POR 70. For any given x-ray with coordinate $(\beta_1, \gamma_1)$, where β is the gantry rotation angle and γ is the detector fan angle, its conjugate ray is located at $$(\beta_2, \gamma_2) = (\pi + \beta_1 + 2\gamma_1, -\gamma_1). \quad (1)$$

Figure 7:
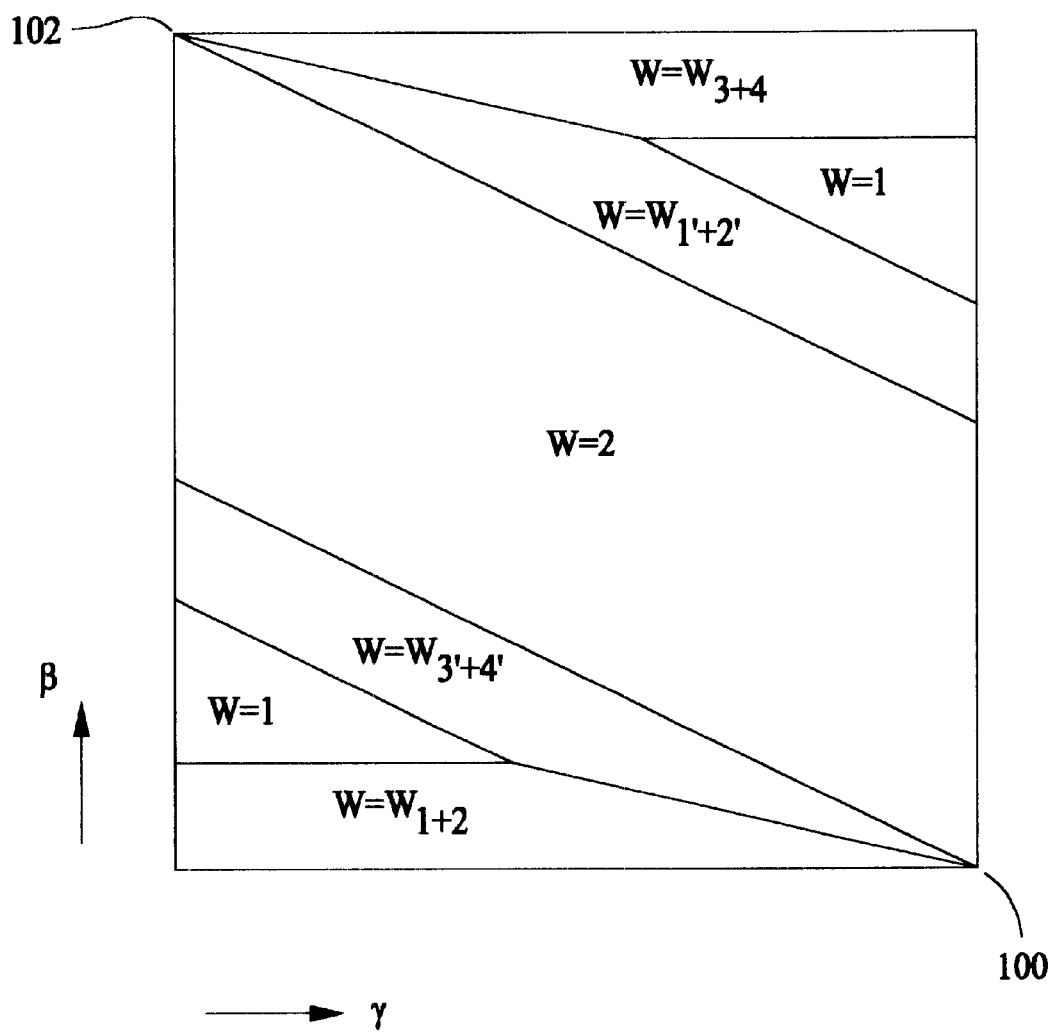
FIG. 7 is a representation of a conjugate weighting function used in one embodiment of the present invention.

Using this equation and the analysis above, a conjugate weighting function is determined, as shown in FIG. 7, where $w_{i+j}$ is the summation of the helical weights for real data rows l and j (i=0, 1, ..., n-2, j=i+1), and it is expressed as:

$$w_{i+j} = w_i + w_j$$

where $w_i$ and $w_j$ are the helical row weights and are defined as:

$$w_t = f(\beta - \beta_t), \quad t = i, j$$

and $$\beta_t = \frac{2\pi}{p} t.$$

Here p is the helical pitch, while $f(\beta - \beta_1)$ is a valid helical weighting function that can be either linear or non-linear functions. One example of linear functions is expressed as:

$$f(x) = \begin{cases} x, & |x| \le \beta_n \\ 0, & |x| > \beta_n \end{cases}$$

while $w_{i'+j'}$ is the conjugate weights correspondent to of the helical weights $w_{i+j}$, which satisfies $$w_{i+j}(\beta_1, \gamma_1) + w_{i'+j'}(\beta_2, \gamma_2) = 2.$$

The row-wise weighting function is nearly smooth and is numerically robust. A computation similar to underscan is used, in one embodiment of the present invention, for a fast hardware implementation of new row-wise algorithm.

In one embodiment of the present invention, a helical weighting is performed first. A resultant weighting function after applying a row-wise weighting $w_o(\beta)$ to data is written as:

$$w_o(\beta) = \begin{cases} \dfrac{\beta}{\beta_p}, & 0 \le \beta \le \beta_p \\ 1, & \beta_p < \beta < \beta_p n \\ \dfrac{\beta_p(n+1) - \beta}{\beta_p}, & \beta_p n \le \beta \le \beta_p(n+1) \end{cases}$$

where: β is a gantry rotation angle;

$$\beta_p = \frac{2\pi}{p};$$

p is a helical pitch used to acquire the projection data; and n is the number of rows of detector channels utilized. In addition, n>1 and p>n.

A conjugate view weighting is applied next. Two lines $L_1$ and $L_2$ are conjugate in Radon space when their coordinates satisfy equation (1) above, where γ denotes a fan angle. Denoting $\beta'_o(\beta,\gamma)$ as the line conjugate to the line β=0, and $\beta_n^c(\beta,\gamma)$ as the line conjugate to $\beta=\beta_p$, the conjugate weights are written:

$$w_c(\beta, \gamma) = \begin{cases} \dfrac{\beta_o^c - \beta}{\beta_p}, & \beta_o^c - \beta_p \le \beta \le \beta_o^c \\ 1, & \beta_n^c + \beta_p < \beta < \beta_o^c - \beta_p \\ \dfrac{\beta - \beta_n^c}{\beta_p}, & \beta_n^c \le \beta \le \beta_n^c + \beta_p. \end{cases}$$

In one embodiment, a combined helical weight and conjugate weight is applied to at least a portion of the acquired projection data to produce virtual projection data compensating for incomplete helical row data of the acquired projection data. The combined weight is applied by separately applying pre-calculated helical weights and pre-calculated conjugate weights. (By "pre-calculated," it is meant that all the weights to be applied to the acquired data are calculated first. Then the weights are applied to the data when and as needed.) In another embodiment, the combined weights are applied as a single weighting function w(β,γ) written $w(\beta,\gamma) = w_o(\beta) + w_c(\beta,\gamma)$.

Using the weights as described above, the run time computation is very simple, and can be described in one embodiment by the following pseudo-code:

```
{
    Pre-calculate helical weights
    Pre-calculate underscan weights
    Generate the final weights
    {
        View=0:n
        Read one view from prepped view buffer
        Vector multiplication with the final weights
        Vector summation with its interpolation pairs
        Write to projection view buffer
    }
}
```

Computer 36 and/or image reconstructor 34 of imaging system 10, either alone or in combination, provide the processing power necessary to perform the computational steps described above in at least one embodiment of the present invention. Instructions for performing the computational steps are stored in an associated memory, such as mass storage device 38, read only or read/write memory (not shown separately in FIG. 1), or media 52.

In at least one embodiment of the present invention, a I computer system separate from imaging system 10 (for example, a workstation, not shown in the figures) is provided to reconstruct images using projection data acquired by imaging system 10. In these embodiments, acquired projection data and corresponding cardiac phase information is transferred from imaging system 10 to the separate computer system via a network (not shown) or suitable media 52. As a free-standing, separate computer system, these embodiments do not require a rotating gantry, a radiation source, or a detector array of their own. Also, these embodiments are configured to read or input projection data previously acquired by a CT imaging system. In other respects, they are configured in manners similar to the other apparatus embodiments discussed herein.

Other embodiments of the present invention include machine-readable media 52 having recorded thereon instructions configured to instruct a computer system to perform steps of one or more of the methods described herein.

It will be appreciated by those skilled in the art that the embodiments of the present invention described herein provide reduced artifact and noise levels, and better slice sensitivity profiles than embodiments employing half scan and partial scan algorithms. Moreover, a nearly smooth weighting function in the y direction is achieved for robust calculation. Furthermore, embodiments of the present invention can be implemented using relatively simple hardware.

While the invention has been described in terms of various specific embodiments, those skilled in the art will recognize that the invention can be practiced with modification within the spirit and scope of the claims.

What is claimed is:

1. A method for imaging an object utilizing a computed tomographic (CT) imaging system having a rotating gantry, a multislice detector array on the rotating gantry and utilizing at least n>1 rows of detector channels, and a radiation source on the rotating gantry configured to project a beam of radiation towards the multislice detector array through an object to be imaged;

said method comprising:
helically scanning the object with the CT imaging system at a pitch p>n to acquire projection data from the n rows of detector channels;
applying a combined helical weight and conjugate weight to at least a portion of the acquired projection data to produce virtual projection data compensating for incomplete helical row data of the acquired projection data; and
reconstructing an image of the object utilizing the acquired projection data and the virtual projection data.

2. A method in accordance with claim 1 wherein said applying a combined helical weight and conjugate weight further comprises pre-calculating helical weights and pre-calculating underscan weights.

3. A method in accordance with claim 2 wherein said applying a combined helical weight and conjugate weight further comprises pre-calculating a combined weight as a sum of the helical weights and the underscan weights.

4. A method in accordance with claim 1 wherein the pre-calculated helical weights $w_o(\beta)$ are written as:

$$w_o(\beta) = \begin{cases} \dfrac{\beta}{\beta_p}, & 0 \le \beta \le \beta_p \\ 1, & \beta_p < \beta < \beta_p n \\ \dfrac{\beta_p(n+1) - \beta}{\beta_p}, & \beta_p n \le \beta \le \beta_p(n+1) \end{cases}$$

where:
$\beta$ is a gantry rotation angle; and $$\beta_p = \frac{2\pi}{p}.$$

5. A method for imaging an object utilizing a computed tomographic (CT) imaging system having a rotating gantry, a multislice detector array on the rotating gantry and utilizing at least n>1 rows of detector channels, and a radiation source on the rotating gantry configured to project a beam of radiation towards the multislice detector array through an object to be imaged;

said method comprising:
helically scanning the object with the CT imaging system at a pitch p>n to acquire projection data from the n rows of detector channels;
applying a combined helical weight and conjugate weight to at least a portion of the acquired projection data to produce virtual projection data compensating for incomplete helical row data of the acquired projection data; and
reconstructing an image of the object utilizing the acquired projection data and the virtual projection data;
wherein the conjugate weights $w_c(\beta,\gamma)$ are written as:

$$w_c(\beta,\gamma) = \begin{cases} \dfrac{\beta_o^c - \beta}{\beta_p}, & \beta_o^c - \beta_p \le \beta \le \beta_o^c \\ 1, & \beta_n^c + \beta_p < \beta < \beta_o^c - \beta_p \\ \dfrac{\beta - \beta_n^c}{\beta_p} & \beta_n^c \le \beta \le \beta_n^c + \beta_p \end{cases}$$

where:
$\beta$ is a gantry rotation angle;
$\gamma$ is a fan angle;

$$\beta_p = \frac{2\pi}{p};$$

$\beta_o^c(\beta,\gamma)$ is a line conjugate to a line $\beta=0$; and
$\beta_n^c(\beta,\gamma)$ is a line conjugate to $\beta=\beta_p$.

6. A method in accordance with claim 5 wherein the pre-calculated helical weights $w_o(\beta)$ are written as:

$$w_o(\beta) = \begin{cases} \dfrac{\beta}{\beta_p}, & 0 \le \beta \le \beta_p \\ 1, & \beta_p < \beta < \beta_p n \\ \dfrac{\beta_p(n+1) - \beta}{\beta_p}, & \beta_p n \le \beta \le \beta_p(n+1) \end{cases}.$$

7. A method in accordance with claim 6 wherein the combined weights are applied as a weight $w(\beta,\gamma)$ written:

$w(\beta,\gamma) = w_o(\beta) + w_c(\beta,\gamma).$

8. A computed tomographic (CT) imaging system having a rotating gantry, a multislice detector array on said rotating gantry and configurable to perform scans utilizing n>1 rows of detector channels, and a radiation source on said rotating gantry configured to project a beam of radiation towards said multislice detector array through an object to be imaged;

said imaging system configured to:
   helically scan the object at a pitch p>n to acquire projection data from said n rows of detector channels;
   apply a combined helical weight and conjugate weight to at least a portion of said acquired projection data to produce virtual projection data compensating for incomplete helical row data of said acquired projection data; and
   reconstruct an image of the object utilizing said acquired projection data and said virtual projection data.

9. An imaging system in accordance with claim 8 wherein to apply said combined helical weight and conjugate weight, said imaging system is further configured to pre-calculate helical weights and pre-calculate underscan weights.

10. An imaging system in accordance with claim 9 wherein to apply said combined helical weight and conjugate weight, said imaging system is further configured to pre-calculate a combined weight as a sum of said helical weights and said underscan weights.

11. An imaging system method in accordance with claim 8 wherein said pre-calculated helical weights $w_o(\beta)$ are written as:

$$w_o(\beta) = \begin{cases} \dfrac{\beta}{\beta_p}, & 0 \le \beta \le \beta_p \\ 1, & \beta_p < \beta < \beta_p n \\ \dfrac{\beta_p(n+1) - \beta}{\beta_p}, & \beta_p n \le \beta \le \beta_p(n+1) \end{cases}$$

where:
   $\beta$ is a gantry rotation angle; and $$\beta_p = \frac{2\pi}{p}.$$

12. A computed tomographic (CT) imaging system having a rotating gantry, a multislice detector array on said rotating gantry and configurable to perform scans utilizing at least n>1 rows of detector channels, and a radiation source on said rotating gantry configured to project a beam of radiation towards said multislice detector array through an object to be imaged;

said imaging system configured to:
   helically scan the object at a pitch p>n to acquire projection data from said n rows of detector channels;
   apply a combined helical weight and conjugate weight to at least a portion of said acquired projection data to produce virtual projection data compensating for incomplete helical row data of said acquired projection data; and
   reconstruct an image of the object utilizing said acquired projection data and said virtual projection data;

wherein said conjugate weights $w_c(\beta,\gamma)$ are written as:

$$w_c(\beta, \gamma) = \begin{cases} \dfrac{\beta_o^c - \beta}{\beta_p}, & \beta_o^c - \beta_p \le \beta \le \beta_o^c \\ 1, & \beta_n^c + \beta_p < \beta < \beta_o^c - \beta_p \\ \dfrac{\beta - \beta_n^c}{\beta_p}, & \beta_n^c \le \beta \le \beta_n^c + \beta_p \end{cases}$$

where:
   $\beta$ is a gantry rotation angle;
   $\gamma$ is a fan angle;

$$\beta_p = \frac{2\pi}{p};$$

$\beta_o^c(\beta,\gamma)$ is a line conjugate to a line $\beta=0$; and
   $\beta_n^c(\beta,\gamma)$ is a line conjugate to $\beta=\beta_p$.

13. An imaging system in accordance with claim 12 wherein said pre-calculated helical weights $w_o(\beta)$ are written as:

$$w_o(\beta) = \begin{cases} \dfrac{\beta}{\beta_p}, & 0 \le \beta \le \beta_p \\ 1, & \beta_p < \beta < \beta_p n \\ \dfrac{\beta_p(n+1) - \beta}{\beta_p}, & \beta_p n \le \beta \le \beta_p(n+1) \end{cases}$$

14. An imaging system in accordance with claim 13 wherein said combined weights are applied as a weight $w(\beta,\gamma)$ written:

$$w(\beta,\gamma) = w_o(\beta) + w_c(\beta,\gamma).$$

15. A computer configured to:

read projection data obtained by helically scanning an object at a pitch p>n utilizing a computed tomographic imaging system using n rows of detector channels;

apply a combined helical weight and conjugate weight to at least a portion of the acquired projection data to produce virtual projection data compensating for incomplete helical row data of the acquired projection data; and reconstruct an image of the object utilizing the acquired projection data and said virtual projection data.

16. A computer in accordance with claim 15 wherein to apply said combined helical weight and conjugate weight, said computer is further configured to pre-calculate helical weights and pre-calculate underscan weights.

17. A computer in accordance with claim 16 wherein to apply said combined helical weight and conjugate weight, said computer is further configured to pre-calculate a combined weight as a sum of said helical weights and said underscan weights.

18. A computer method in accordance with claim 15 wherein said pre-calculated helical weights $w_o(\beta)$ are written as:

$$w_o(\beta) = \begin{cases} \dfrac{\beta}{\beta_p}, & 0 \leq \beta \leq \beta_p \\ 1, & \beta_p < \beta < \beta_p n \\ \dfrac{\beta_p(n+1) - \beta}{\beta_p}, & \beta_p n \leq \beta \leq \beta_p(n+1) \end{cases}$$

where:
$\beta$ is a gantry rotation angle; and $$\beta_p = \frac{2\pi}{p}.$$

19. A computer in accordance with claim 15 wherein said conjugate weights $w_c(\beta,\gamma)$ are written as:

$$w_c(\beta, \gamma) = \begin{cases} \dfrac{\beta_o^c - \beta}{\beta_p}, & \beta_o^c - \beta_p \leq \beta \leq \beta_o^c \\ 1, & \beta_n^c + \beta_p < \beta < \beta_o^c - \beta_p \\ \dfrac{\beta - \beta_n^c}{\beta_p}, & \beta_n^c \leq \beta \leq \beta_n^c + \beta_p \end{cases}$$

where:
$\beta$ is a gantry rotation angle;
$\gamma$ is a fan angle;

$$\beta_p = \frac{2\pi}{p};$$

$\beta_o^c(\beta,\gamma)$ is a line conjugate to a line $\beta=0$; and
$\beta_o^i(\beta,\gamma)$ is a line conjugate to $\beta=\beta_p$.

20. A computer system in accordance with claim 19 wherein said pre-calculated helical weights $w_o(\beta)$ are written as:

$$w_o(\beta) = \begin{cases} \dfrac{\beta}{\beta_p}, & 0 \leq \beta \leq \beta_p \\ 1, & \beta_p < \beta < \beta_p n \\ \dfrac{\beta_p(n+1) - \beta}{\beta_p}, & \beta_p n \leq \beta \leq \beta_p(n+1) \end{cases}.$$

21. A computer in accordance with claim 20 wherein said combined weights are applied as a weight $w(\beta,\gamma)$ written:

$$w(\beta,\gamma) = w_o(\beta) + w_c(\beta,\gamma).$$

22. A computer readable medium having recorded thereon instructions configured to instruct a computer to:
read projection data acquired by helically scanning an object at a pitch p>n utilizing a computed tomographic imaging system using n rows of detector channels;
apply a combined helical weight and conjugate weight to at least a portion of the acquired projection data to produce virtual projection data compensating for incomplete helical row data of the acquired projection data; and
reconstruct an image of the object utilizing the acquired projection data and said virtual projection data.

23. A computer readable medium in accordance with claim 22 wherein to apply said combined helical weight and conjugate weight, said computer readable medium has recorded thereon instructions configured to instruct the computer to pre-calculate helical weights and pre-calculate underscan weights.

24. A computer readable medium in accordance with claim 23 wherein to apply said combined helical weight and conjugate weight, said computer readable medium has recorded thereon instructions configured to instruct the computer to pre-calculate a combined weight as a sum of said helical weights and said underscan weights.

25. A computer readable medium in accordance with claim 22 wherein said pre-calculated helical weights $w_o(\beta)$ are written as:

$$w_o(\beta) = \begin{cases} \dfrac{\beta}{\beta_p}, & 0 \leq \beta \leq \beta_p \\ 1, & \beta_p < \beta < \beta_p n \\ \dfrac{\beta_p(n+1) - \beta}{\beta_p}, & \beta_p n \leq \beta \leq \beta_p(n+1) \end{cases}$$

where:
$\beta$ is a gantry rotation angle; and $$\beta_p = \frac{2\pi}{p}.$$

26. A computer readable medium in accordance with claim 22 wherein said conjugate weights $w_c(\beta,\gamma)$ are written as:

$$w_c(\beta, \gamma) = \begin{cases} \dfrac{\beta_o^c - \beta}{\beta_p}, & \beta_o^c - \beta_p \leq \beta \leq \beta_o^c \\ 1, & \beta_n^c + \beta_p < \beta < \beta_o^c - \beta_p \\ \dfrac{\beta - \beta_n^c}{\beta_p}, & \beta_n^c \leq \beta \leq \beta_n^c + \beta_p \end{cases}$$

where:
$\beta$ is a gantry rotation angle;
$\gamma$ is a fan angle;

$$\beta_p = \frac{2\pi}{p};$$

$\beta_o^c(\beta,\gamma)$ is a line conjugate to a line $\beta=0$; and
$\beta_o^c(\beta,\gamma)$ is a line conjugate to $\beta=\beta_p$.

27. A computer readable medium in accordance with claim 26 wherein said pre-calculated helical weights $w_o(\beta)$ are written as:

$$w_o(\beta) = \begin{cases} \dfrac{\beta}{\beta_p}, & 0 \leq \beta \leq \beta_p \\ 1, & \beta_p < \beta < \beta_p n \\ \dfrac{\beta_p(n+1) - \beta}{\beta_p}, & \beta_p n \leq \beta \leq \beta_p(n+1) \end{cases}$$

28. A computer readable medium in accordance with claim 27 wherein said combined weights are applied as a weight $w(\beta,\gamma)$ written:

$$w(\beta,\gamma) = w_o(\beta) + w_c(\beta,\gamma).$$

* * * * *

UNITED STATES PATENT AND TRADEMARK OFFICE
CERTIFICATE OF CORRECTION

PATENT NO. : 6,490,334 B1
DATED : December 3, 2002
INVENTOR(S) : Wang et al.

It is certified that error appears in the above-identified patent and that said Letters Patent is hereby corrected as shown below:

Column 8,
Line 34, delete "$w_o(\beta,\gamma)$" and insert therefor -- $w_c(\beta,\gamma)$ --.

Line 50, delete "$\beta_o^c(\beta,\gamma)$ is a line conjugate to a line" and insert therefor -- $\beta_o^c(\beta,\gamma)$ is a line conjugate to a line --

Line 51, delete "$\beta_o^c(\beta,\gamma)$ is a line conjugate to $\beta=\beta_p$" and insert therefor -- $\beta_n^c(\beta,\gamma)$ is a line conjugate to $\beta=\beta_p$ --.

Column 10,
Line 20, delete "$\beta_o^c(\beta,\gamma)$ is a line conjugate to $\beta=\beta_p$" and insert therefor -- $\beta_n^c(\beta,\gamma)$ is a line conjugate to $\beta=\beta_p$ --.

Line 37, delete "$w_o(\beta,\gamma)$" and insert therefor -- $w_c(\beta,\gamma)$ --.

Column 11,
Line 35, delete "$\beta_o^i(\beta,\gamma)$ is a line conjugate to $\beta=\beta_p$" and insert therefor -- $\beta_n^c(\beta,\gamma)$ is a line conjugate to $\beta=\beta_p$ --.

Column 12,
Line 29, delete "$w_o(\beta,\gamma)$" and insert therefor -- $w_c(\beta,\gamma)$ --.

Line 48, delete "$\beta_o^c(\beta,\gamma)$ is a line conjugate to $\beta=\beta_p$" and insert therefor -- $\beta_n^c(\beta,\gamma)$ is a line conjugate to $\beta=\beta_p$ --.

Signed and Sealed this

Nineteenth Day of April, 2005

JON W. DUDAS
*Director of the United States Patent and Trademark Office*